(12) United States Patent
Chmielewski et al.

(10) Patent No.: US 6,710,224 B2
(45) Date of Patent: Mar. 23, 2004

(54) SUPERABSORBENT POLYMERS PROVIDING LONG-TERM GENERATION OF FREE VOLUME IN PARTIALLY HYDRATED ABSORBENT CORES

(75) Inventors: Harry J. Chmielewski, Brunswick, GA (US); Andrew Baker, Lawrenceville, GA (US)

(73) Assignee: Paragon Trade Brands, Norcross, GA (US)

( * ) Notice: Subject to any disclaimer, the term of this patent is extended or adjusted under 35 U.S.C. 154(b) by 0 days.

(21) Appl. No.: 09/828,846

(22) Filed: Apr. 10, 2001

(65) Prior Publication Data

US 2002/0035353 A1 Mar. 21, 2002

Related U.S. Application Data

(63) Continuation-in-part of application No. 09/686,822, filed on Oct. 12, 2000, and a continuation-in-part of application No. 09/685,608, filed on Oct. 11, 2000.
(60) Provisional application No. 60/163,393, filed on Nov. 4, 1999, and provisional application No. 60/161,417, filed on Oct. 25, 1999.

(51) Int. Cl.[7] ................................................ A61F 13/15
(52) U.S. Cl. ...................................................... 604/368
(58) Field of Search ............................ 604/367–8, 368, 604/359

(56) References Cited

U.S. PATENT DOCUMENTS

| 3,661,875 A | 5/1972 | Sieja |
| 4,076,663 A | 2/1978 | Masuda et al. |
| 4,093,776 A | 6/1978 | Aoki et al. |
| 4,541,871 A | 9/1985 | Obayashi et al. |
| 4,587,308 A | 5/1986 | Makita et al. |
| 4,625,001 A | 11/1986 | Tsubakimoto et al. |
| 4,654,039 A | 3/1987 | Brandt et al. |
| 4,666,983 A | 5/1987 | Tsubakimoto et al. |
| 4,673,402 A | 6/1987 | Weisman et al. |
| 4,734,478 A | 3/1988 | Tsubakimoto et al. |
| 4,789,861 A | 12/1988 | Baggett et al. |
| 4,824,901 A | 4/1989 | Alexander et al. |
| 4,834,735 A | 5/1989 | Alemany et al. |
| 5,147,343 A | 9/1992 | Kellenberger |
| 5,164,459 A | 11/1992 | Kimura et al. |
| 5,279,854 A | 1/1994 | Kendall et al. |
| 5,281,207 A | 1/1994 | Chmielewski et al. |
| 5,330,822 A | 7/1994 | Berg et al. |
| 5,364,380 A | * 11/1994 | Tanzer et al. ................ 604/358 |
| 6,046,377 A | * 4/2000 | Huntoon et al. ............. 604/358 |
| 6,072,101 A | 6/2000 | Beihoffer et al. |
| 6,133,193 A | * 10/2000 | Kajikawa et al. ............ 428/402 |
| 6,235,965 B1 | * 5/2001 | Beihoffer et al. ............ 604/367 |

FOREIGN PATENT DOCUMENTS

| DE | 4020780 | 8/1991 |
| EP | 0032649 | 7/1981 |
| EP | 0509708 | 10/1992 |
| WO | 90/08789 | 8/1990 |
| WO | 92/16565 | 10/1992 |
| WO | 93/05080 | 3/1993 |

* cited by examiner

Primary Examiner—Weilun Lo
Assistant Examiner—Catharine L Anderson
(74) Attorney, Agent, or Firm—Hunton & Williams LLP

(57) ABSTRACT

An absorbent composition providing unexpectedly high fluid capacity with minimal gel-blocking, articles comprising the absorbent composition and methods of preparing the absorbent composition are disclosed. The absorbent composition optionally comprises a surface crosslinked polymer disbursed within a fibrous matrix of wettable fibers. The surface crosslinked polymer has an FVAUL value of at least about 60 cc after 10 minutes.

70 Claims, 8 Drawing Sheets

SUPERABSORBENT POLYMERS PROVIDING LONG-TERM GENERATION OF FREE VOLUME IN PARTIALLY HYDRATED ABSORBENT CORES

RELATED APPLICATIONS

This is a CIP of U.S. patent applications Ser. No. 09/686,822 (filed Oct. 12, 2000 based on 60/163,393 filed Nov. 4, 1999) and 09/685,608 (filed Oct. 11, 2000 based on 60/161,417 filed Oct. 25, 1999).

FIELD OF INVENTION

The present invention relates generally to an absorbent composition for absorbent articles such as diapers, incontinence products, training pants, sanitary napkins, and the like. In particular, the present invention is directed to an absorbent composition having unexpectedly high fluid capacity and minimal gel-blocking properties, an absorbent article comprising said absorbent composition and a method of preparing the absorbent composition.

BACKGROUND OF THE INVENTION

Absorbent materials that can absorb large amounts of liquids, such as water or body exudates, have many applications in disposable absorbent articles such as baby diapers, sanitary napkins, wound dressings, bandages, incontinent pads, and the like. Much effort has been expended to find cost-effective materials for absorbent articles which display good liquid absorbency and retention. Superabsorbent polymers ("SAPs") in the form of granules, beads, fibers, bits of film, globules, etc. have been favored for such purposes. Such SAPs are generally water-insoluble and water-swellable substances capable of absorbing fluids in an amount which is at least ten times the weight of the substances in their dry form.

In one type of SAP, the particles or fibers may be described chemically as a crosslinked, sodium-neutralized polyacrylate. Included in this class of materials are such modified polymers as sodium-neutralized crosslinked polyacrylates and polysaccharides including, for example, cellulose, starch and regenerated cellulose which are modified to be carboxylated, phosphonoalkylated, sulphoxylated or phosphorylated, causing the SAP to be highly hydrophilic. Such modified polymers may also be crosslinked to reduce their water solubility.

The water absorption and water retention characteristics of SAPs are due to the presence in the polymer structure of ionizable functional groups. These ionizable functional groups are usually carboxyl groups, a high proportion of which are in the salt form when the polymer is dry but which undergo dissociation upon contact with water. In the dissociated state, the polymer chain will have a series of functional groups attached to it, wherein the groups have the same electric charge and thus repel one another. This leads to expansion of the polymer structure which, in turn, permits further absorption of water molecules although this expansion is subject to the constraints provided by the cross-links in the polymer structure which must be sufficient to prevent dissolution of the polymer.

The degree of cross-linking of superabsorbent polymers can be an important factor in establishing their absorbent capacity and gel strength. Absorbent polymers useful in absorbent articles generally need to have adequately high sorption capacity, as well as adequately high gel strength. Gel strength relates to the tendency of the swollen polymer to deform under an applied stress. If gel strength is low, the polymer can deform to such an extent so as to fill the capillary void spaces in the absorbent material to an unacceptable degree, thereby inhibiting the rate of fluid uptake or the fluid distribution by the absorbent material. Such gel deformation is generally referred to as "gel-blocking."

Once gel-blocking occurs, further fluid uptake or distribution takes place primarily via a slow diffusion process. In practical terms, this means that gel-blocking can substantially impede the distribution of fluids to relatively dry zones or regions of the absorbent material. Thus, leakage from an absorbent article including the absorbent material can take place well before the particles of absorbent polymer in the absorbent material are fully saturated or before the fluid can diffuse or wick past the "blocking" polymer into the rest of the absorbent material.

In general, increasing gel strength will result in an increase in the permeability of an absorbent material comprising swollen absorbent polymer. However, this typically also reduces the absorbent capacity of the gel undesirably. See, for example, U.S. Pat. No. 4,654,039 to Brandt et al. and U.S. Pat. No. 4,834,735 to Alemany et al.

This gel-blocking phenomenon has typically necessitated the use of a fibrous matrix in which are dispersed the particles of absorbent polymer. This fibrous matrix keeps the particles of absorbent polymer separated from one another and provides a capillary structure that allows fluid to reach the absorbent polymer located in regions remote from the initial fluid discharge point. See U.S. Pat. No. 4,834,735 to Alemany et al.

As is apparent from the foregoing, each of the above references, presents a variety of means for preparing absorbent materials. However, all of these proposed means are deficient in terms of effectiveness and low product quality, mechanical complexity in design, and/or associated cost inefficiencies. For example, dispersing the absorbent polymer in a fibrous matrix at relatively low concentrations in order to minimize or avoid gel-blocking can significantly increase the bulkiness of the absorbent article or lower the overall fluid storage capacity of thinner absorbent structures.

In view of the deficiencies of the various products and processes disclosed in the above references, it is highly desirable to provide an absorbent composition that is superior in fluid capacity and gel-blocking properties. It is also highly desirable to provide an absorbent article comprising said absorbent composition and a method of preparing the absorbent composition.

SUMMARY OF THE INVENTION

In general, the present invention is directed to an absorbent composition that has an unexpectedly high fluid capacity, also referred to as absorptive capacity, and minimal gel-blocking properties, as well as absorbent articles comprising the absorbent composition and methods of preparing the absorbent composition. More particularly, the absorbent composition of the present invention has a Finite Volume Absorption Under Load ("FVAUL") value of at least about 60 cc after 10 minutes.

One embodiment of the present invention is an absorbent composition comprising: about 5% by weight to about 30% by weight of a fibrous matrix comprising wettable fibers and about 70% by weight to about 95% by weight of a surface crosslinked polymer having a FVAUL value of at least about 60 cc after 10 minutes, said surface crosslinked polymer being disbursed within said fibrous matrix.

A further embodiment of the present invention is an absorbent composition prepared by the process comprising:

providing a first layer of wettable fibers; distributing on the first layer of wettable fibers a layer of surface crosslinked polymer having a FVAUL value of at least about 60 cc after 10 minutes; providing a second layer of wettable fibers on top of the layer of surface crosslinked polymer; and calendaring said layers to form the wettable fibers into a fibrous matrix having the surface crosslinked polymer disbursed therein, said surface crosslinked polymer comprising about 70% by weight to about 95% by weight the absorbent composition and said wettable fibers comprising about 5% by weight to about 30% by weight of the absorbent composition.

An even further embodiment of the present invention is an absorbent composition comprising: a surface crosslinked polymer having a FVAUL value of at least about 60 cc after 10 minutes.

An still further embodiment of the present invention is an absorbent article comprising: a permeable topsheet; a substantially impermeable backsheet; and an absorbent core disposed between the permeable topsheet and the substantially impermeable backsheet, said absorbent core comprising an absorbent composition comprising about 5% by weight to about 30% by weight of a fibrous matrix comprising wettable fibers and about 70% by weight to about 95% by weight of a surface crosslinked polymer having a FVAUL value of at least about 60 cc after 10 minutes, said surface crosslinked polymer being disbursed within said fibrous matrix.

Yet a further embodiment of the present invention is a method for preparing an absorbent composition comprising: providing a first layer of wettable fibers; distributing on the first layer of wettable fibers a layer of surface crosslinked polymer having a FVAUL value of at least about 60 cc after 10 minutes; providing a second layer of wettable fibers on top of the layer of surface crosslinked polymer; and calendaring said layers to form the wettable fibers into a fibrous matrix having the surface crosslinked polymer disbursed therein, said surface crosslinked polymer comprising about 70% by weight to about 95% by weight the absorbent composition and said wettable fibers comprising about 5% by weight to about 30% by weight of the absorbent composition.

These and other aspects of the invention will become apparent to those of ordinary skill in the art from the following description.

DETAILED DESCRIPTION OF THE INVENTION

Figure 1:
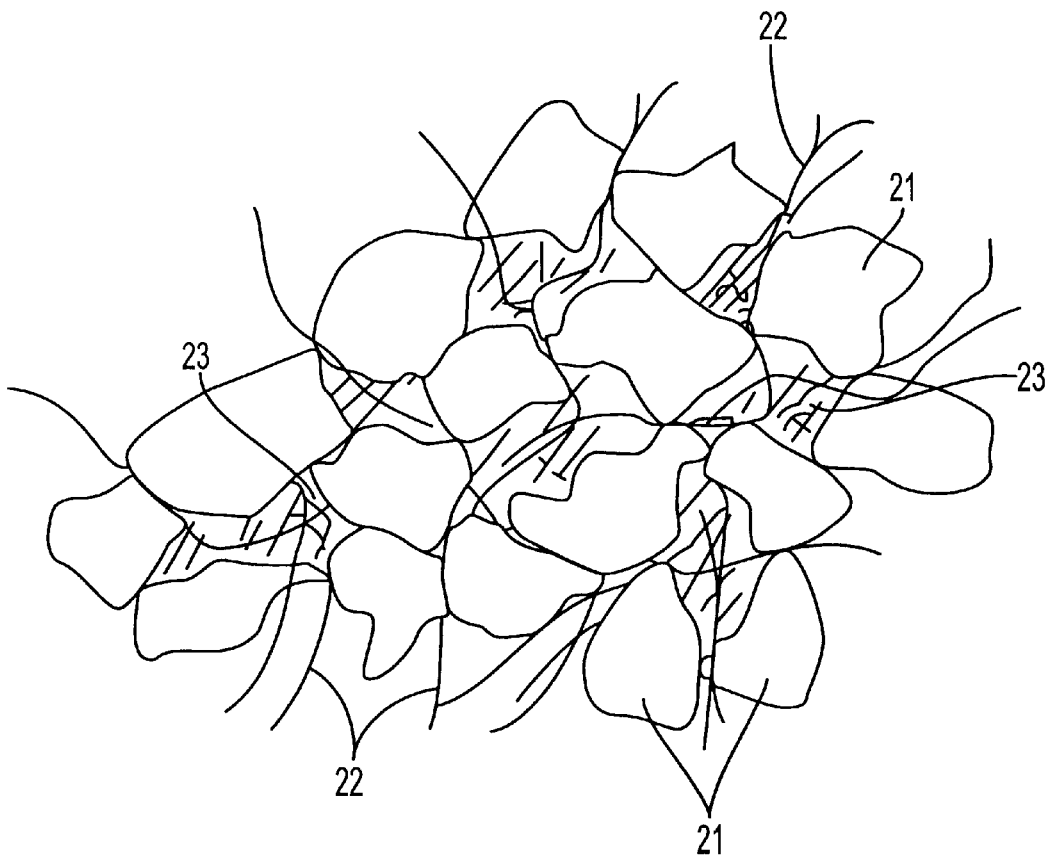
FIG. 1 is a pictorial representation of a cross-sectional portion of an absorbent composite according to an implementation of present invention.

The present invention relates, in part, to absorbent compositions comprising polymers that exhibit an unexpectedly high fluid capacity, also referred to as absorptive capacity, and minimal gel blocking properties. In an implementation of the present invention, an absorbent composition is provided that comprises: a surface crosslinked polymer having a FVAUL value of at least about 60 cc after 10 minutes. The surface crosslinked polymer of the present invention has an FVAUL value of preferably at least about 65 cc after 10 minutes, even more preferably of at least about 70 cc after 10 minutes and most preferably of at least about 75 cc after 10 minutes.

This type of surface crosslinked polymer continues to generate free volume within the hydrated gel for times much greater than the times observed for current conventional polymers. The surface crosslinked polymer preferably permits the absorbent composition to achieve equilibrium swelling levels within about 5 minutes to about 10 minutes after a third dose of urine. Further, the surface crosslinked polymer preferably achieves equilibrium swelling levels at an FVAUL value of no less than about 75 cc. Additionally, the absorbent composition may continue to swell at a substantially constant rate for at least about 4 hours after a third dose of urine at a finite volume of urine absorption.

Absorbent compositions in accordance with an implementation of the present invention provide unexpectedly high fluid capacity. In accordance with certain implementations of the present invention, minimal gel-blocking and high resistance to urine degradation is provided. Absorbent articles, such as diapers, for example without limitation, containing the absorbent composition of the present invention provide reduced overnight urine leakage.

The absorbent polymers useful in the present invention can be formed by any polymerization and/or crosslinking techniques. Typical processes for producing these polymers are described in U.S. Reissue Pat. No. 32,649 (Brandt et al.), issued Apr. 19, 1988, U.S. Pat. No. 4,666,983 (Tsubakimoto et al.), issued May 19, 1987, and U.S. Pat. No. 4,625,001 (Tsubakimoto et al.), issued Nov. 25, 1986, all of which are incorporated by reference. Crosslinking can be effected during polymerization by incorporation of suitable crosslinking monomers. Alternatively, the polymers can be crosslinked after polymerization by reaction with a suitable reactive crosslinking agents. Surface crosslinking of the initially formed polymers is a preferred process for obtaining absorbent polymers having relatively high fluid capacity with minimal gel-blocking properties.

Without being bound by theory, it is believed that surface crosslinking increases the resistance to deformation of the surfaces of swollen absorbent polymer particles, thus reducing the degree of contact between neighboring polymer particles when the swollen particles are deformed under an external pressure. Surface crosslinked polymers have a higher level of crosslinking in the vicinity of the surface than in the interior. As used herein, "surface" describes the outer-facing boundaries of the particle. For porous absorbent polymers (e.g., porous particles, etc.), exposed internal boundaries can also be included. By a higher level of crosslinking at the surface, it is meant that the level of functional crosslinks for the absorbent polymer in the vicinity of the surface is generally higher than the level of functional crosslinks for the polymer in the interior. The gradation in crosslinking from surface to interior can vary, both in depth and profile. Surface crosslinked polymers and methods of making them are described in U.S. Pat. Nos. 4,666,983 and 4,734,478 issued to Tsubakimoto et al. and which are incorporated herein by reference for all purposes.

A number of processes for introducing surface crosslinks are disclosed in the art. Suitable methods for surface crosslinking include those where (i) a di- or poly-functional reagent(s) capable of reacting with existing functional groups within the absorbent polymer is applied to the surface of the absorbent polymer; (ii) a di- or poly-functional reagent that is capable of reacting with other added reagents and possibly existing functional groups within the absorbent polymer such as to increase the level of crosslinking at the surface is applied to the surface (e.g., the addition of monomer plus crosslinker and the initiation of a second polymerization reaction); (iii) no additional poly-functional reagents are added, but additional reaction(s) is induced amongst existing components within the absorbent polymer either during or after the primary polymerization process such as to generate a higher level of crosslinking at or near the surface (e.g., suspension polymerization processes wherein the crosslinker is inherently present at higher levels near the surface); and (iv) other materials are added to the surface such as to induce a higher level of crosslinking or otherwise reduce the surface deformability of the resultant hydrogel. Suitable general methods for carrying out surface crosslinking of absorbent polymers according to the present invention are disclosed in U.S. Pat. No. 4,541,871 (Obayashi), issued Sep. 17, 1985; published PCT application WO92/16565 (Stanley), published Oct. 1, 1992, published PCT application WO90/08789 (Tai), published Aug. 9, 1990; published PCT application WO93/05080 (Stanley), published Mar. 18, 1993; U.S. Pat. No. 4,824,901 (Alexander), issued Apr. 25, 1989; U.S. Pat. No. 4,789,861 (Johnson), issued Jan. 17, 1989; U.S. Pat. No. 4,587,308 (Makita), issued May 6, 1986; U.S. Pat. No. 4,734,478 (Tsubakimoto), issued Mar. 29, 1988; U.S. Pat. No. 5,164,459 (Kimura et al.), issued Nov. 17, 1992; published German patent application 4,020,780 (Dahmen), published Aug. 29, 1991; and published European patent application 509,708 (Gartner), published Oct. 21, 1992; all of which are incorporated herein by reference. For cationic absorbent polymers, suitable di- or poly-functional crosslinking reagents include di/poly-haloalkanes, di/poly-epoxides, di/poly-acid chlorides, di/poly-tosyl, alkanes di/poly-aldehydes, di/poly-acids, and the like.

Persons of ordinary skill in the art would readily understand how to prepare surface crosslinked polymers in accordance with the present invention without undue experimentation, using conventional techniques and materials, based upon the guidance provided herein.

The surface crosslinked polymer may be nonpolar, unipolar or bipolar. Preferably, the surface crosslinked polymer is bipolar. Persons of skill in the art would be readily able to identify, select and incorporate such polymers in various implementations of the present invention based upon the guidance provided herein. The surface crosslinked polymer incorporated into various implementations preferably provides minimal gel-blocking properties upon absorption of liquid.

The polymers may be lightly crosslinked by including the appropriate amount of a suitable crosslinking monomer during the polymerization reaction. Examples of crosslinking monomers include N,N'-methylenebisacrylamide, ethylene glycol di(meth)acrylate, trimethylolpropane tri(meth)acrylate, triallylamine, diaziridine compounds, acrylic acid and the like. Alternatively, the polymers can be crosslinked after polymerization by reaction with a suitable crosslinking agent such as alkylenebisacylamides, di- or poly-halogenated compounds and/or di- or poly-epoxy compounds. Examples include, methylenebisacrylamide, diiodopropane, dichloropropane, ethylene glycol diglycidyl ether, and the like. The crosslinks may be homogeneously distributed throughout the polymer, or may be preferentially concentrated at or near the surface of the polymer to form surface crosslinked polymer.

Examples of polymers suitable for use herein include those which are prepared from polymerizable, acid-containing monomers, or monomers containing functional groups which can be converted to acid groups after polymerization, without limitation. Thus, such monomers include olefinically unsaturated carboxylic acids and anhydrides, and mixtures thereof. The cation-exchange polymers can also comprise polymers that are not prepared from olefinically unsaturated monomers. Examples of such polymers include polysaccharide-based polymers such as carboxymethyl starch and carboxymethyl cellulose, and poly(amino acid) based polymers such as poly(aspartic acid), without limitation.

Some non-acid monomers can also be included, usually in minor amounts, in preparing the absorbent polymers herein. Such non-acid monomers can include, for example, monomers containing the following types of functional groups: carboxylate or sulfonate esters, hydroxyl groups, amide-groups, amino groups, nitrile groups, quaternary ammonium salt groups, and aryl groups (e.g., phenyl groups, such as those derived from styrene monomer). Other optional non-acid monomers include unsaturated hydrocarbons such as ethylene, propylene, 1-butene, butadiene, and isoprene.

Olefinically unsaturated carboxylic acid and anhydride monomers include the acrylic acids typified by acrylic acid itself, methacrylic acid, α-chloroacrylic acid, α-cyanoacrylic acid, β-methylacrylic acid (crotonic acid), α-phenylacrylic acid, β-acryloxypropionic acid, sorbic acid, α-chlorosorbic acid, angelic acid, cinnamic acid, β-chlorocinnamic acid, β-stearylacrylic acid, itaconic acid, citroconic acid, mesaconic acid, glutaconic acid, aconitic acid, maleic acid, fumaric acid, tricarboxyethylene, and maleic anhydride.

Preferably, the surface crosslinked polymer of the present invention is poly(acrylic acid). More preferably, the surface crosslinked polymer comprises about 95% by weight of poly(acrylic acid) and about 3% by weight of a crosslinking agent. Even more preferably, the crosslinking agent is methylenebisacrylamide. Preferably, the surface crosslinked polymer additionally comprises a neutralizing agent. More preferably, the neutralizing agent is triethanol amine. Persons of skill in the art would readily be able to prepare such surface crosslinked polymers in accordance with implementations of the present invention, using conventional methods and techniques, based upon the guidance provided herein.

In an implementation of the present invention, the superabsorbent polymer can be in the form of a mixed-bed ion-exchange composition which comprises an anion-exchange absorbent polymer and a cation-exchange absorbent polymer. Alternatively, the mixed-bed ion-exchange composition can include a combination of an undemeutralized superabsorbent polymer ("uSAP") in which at least about 30% of the function groups are in free acid form and an anion exchange material. The polymers are also surface-crosslinked polymers in accordance with an implementation of the present invention.

The anion-exchange absorbent polymer will generally contain weak-base groups and will typically be lightly crosslinked polymers which contain a multiplicity of base functional groups, such as primary, secondary and/or tertiary amines, or phosphines. When used as part of a mixed-bed ion-exchange composition, the anion-exchange absorbent polymer can be present in the composition in an amount ranging from about 50% to about 100%, preferably about 80% to about 100%, more preferably from about 90% to about 100%, in the un-neutralized base form. Nonlimiting exemplary polymers suitable for use herein include those which are prepared from polymerizable monomers that contain base groups, or groups which can be converted to base groups after polymerization. Thus, such monomers include those which contain primary, secondary or tertiary amines, or phosphines. Representative monomers include, but are not limited to, ethylenimine (aziridine), allylamine, diallylamine, 4-aminobutene, alkyl oxazolines, vinylformamide, 5-aminopentene, carbodiimides, formaldazine, melamine, and the like, as well as their secondary or tertiary amine derivatives.

Some monomers which do not contain base groups can also be included, usually in minor amounts, in preparing the anion-exchange absorbent polymers herein. The absorbent polymers described herein can be homopolymers, copolymers (including terpolymers and higher order copolymers), or mixtures (blends) of different homopolymers or copolymers. The polymers may also be random, graft, or block copolymers, and may have linear or branched architectures.

While the anion-exchange absorbent polymer is preferably of one type (i.e., homogeneous), mixtures of anion-exchange polymers can also be used in the present invention. For example, mixtures of crosslinked polyethylenimine and crosslinked polyallylamine can be used in the present invention.

Absorbent polymers useful as cation exchanger(s) typically have a multiplicity of acid functional groups such as carboxylic acid groups. When used as part of a mixed-bed ion-exchange composition, the cation-exchange absorbent polymer starts off from about 50% to about 100%, preferably about 80% to about 100%, more preferably from about 90% to about 100%, in the un-neutralized acid form.

Preferred cation-exchange absorbent polymers contain carboxyl groups. These polymers include hydrolyzed starch-acrylonitrile graft copolymers, partially neutralized hydrolyzed starch-acrylonitrile graft copolymers, starch-acrylic acid graft copolymers, partially neutralized starch-acrylic acid graft copolymers, hydrolyzed vinyl acetate-acrylic ester copolymers, hydrolyzed acrylonitrile or acrylamide copolymers, slightly network crosslinked polymers of any of the foregoing copolymers, polyacrylic acid, and slightly network crosslinked polymers of polyacrylic acid. These polymers can be used either solely or in the form of a mixture of two or more different polymers. Examples of these polymer materials are disclosed in U.S. Pat. No. 3,661,875, U.S. Pat. No. 4,076,663, U.S. Pat. No. 4,093,776, U.S. Pat. No. 4,666,983, and U.S. Pat. No. 4,734,478.

Preferably, the polymer is selected from the slightly network crosslinked polymers of polyacrylic acids and starch derivatives thereof. Network crosslinking renders the polymer substantially water-insoluble and, in part, determines the absorptive capacity and extractable polymer content characteristics of the absorbent polymers. Processes for network crosslinking these polymers and typical network crosslinking agents are described in greater detail in U.S. Pat. No. 4,076,663.

While the cation-exchange absorbent polymer is preferably of one type (i.e., homogeneous), mixtures of cation-exchange polymers can also be used in the present invention. For example, mixtures of starch-acrylic acid graft copolymers and slightly network crosslinked polymers of polyacrylic acid can be used in the present invention.

The equivalents of anionic and cationic exchange capacity may be equal or different in the mixed-bed ion-exchange absorbent polymer composition. For example, it may be desirable to have somewhat more equivalents of anionic or cationic ion-exchange absorbent polymer, e.g., to compensate for differences in pK, to compensate for differences in neutralization, to alter the pH of (for example to acidify) the ion-exchanged urine, etc.

Polymerization methods to prepare ion-exchange polymers useful in the present invention can include free radical, ring-opening, condensation, anionic, cationic, or irradiation techniques. The polymer may be prepared in the neutralized, partially neutralized, or un-neutralized form, even though the desired product is at least partially un-neutralized. The absorbent polymer may be prepared using a homogeneous solution polymerization process, or by multi-phase polymerization techniques such as inverse emulsion or suspension polymerization procedures.

U.S. Pat. No. 5,147,343 issued to Kellenberger, U.S. Pat. No. 4,673,402 issued to Weisman, U.S. Pat. No. 5,281,207 issued to Chmielewski et al., and U.S. Pat. No. 4,834,735 issued to Alemany, et al. disclose many types of polymers and methods for making them, and are incorporated herein by reference for all purposes and in a manner that is consistent herewith. Superabsorbenit polymers (SAPs) and methods of making them are described in U.S. Pat. Nos. 4,666,983 and 4,734,478 issued to Tsubakimoto et al. which are incorporated herein by reference for all purposes and in a manner that is consistent herewith. Also, U.S. Pat. No. 5,281,207 to Chmielewski, et al. generally discloses methods and materials for making an absorbent article and is also incorporated herein by reference for all purposes and in a manner that is consistent herewith.

The absorbent material of the invention can optionally include wettable fibers. Preferably, the wettable fibers form a fibrous matrix (or structure) in which the surface crosslinked polymer is disbursed. Methods of preparing such a fibrous matrix are disclosed in U.S. Pat. No. 5,281,207 to Chmielewski, et al., which is incorporated herein by reference for all purposes. The polymer composition is preferably combined with the wettable fibers in an amount from about 70% to about 95% by weight based on the combined weight of fibers and polymer composition by means suitable to distribute the polymer composition therein trying to form a substantially continuous phase of polymer.

Preferably, about 70% by weight to about 95% by weight of the absorbent composition is comprised of a surface crosslinked polymer, in accordance with an implementation of the present invention. More preferably, the surface crosslinked polymer constitutes about 85% by weight to about 95% by weight of the combined weight of the fiberous matrix and the surface crosslinked polymer. Even more preferably, the surface crosslinked polymer constitutes about 90% by weight to about 95% by weight of the combined weight of the fiberous matrix and the surface crosslinked polymer.

Preferably, about 5% by weight to about 30% by weight of the absorbent composition is comprised of a fibrous matrix comprising wettable fibers. More preferably, the wettable fibers constitute about 5% by weight to about 15% by weight of the combined weight of the fiberous matrix and the surface crosslinked polymer. Even more preferably, the wettable fibers constitute about 5% by weight to about 10% by weight of the combined weight of the fiberous matrix and the surface crosslinked polymer.

Preferably, the FVAUL free volume of the absorbent composition is about 20% to about 70%. More preferably, the FVAUL free volume of the absorbent composition is about 20% to about 60%. Even more preferably, the FVAUL free volume of the absorbent composition is about 20% to about 50%. Most preferably, the FVAUL free volume of the absorbent composition is about 25% to about 50%.

Generally, it is desirable to place the polymer somewhat evenly distributed throughout the absorbent composition or composite. Preferably, the surface crosslinked polymer is evenly disbursed within the fibrous matrix.

The wettable fibers can include, but are not limited to, natural fibers, synthetic fibers or combinations thereof. Non-limiting exemplary fibers include wood pulp (fluff), cotton linters, synthetic fibers and mixtures thereof, preferably wood pulp fluff or a mixture of wood pulp, synthetic fibers, and combinations thereof. Non-limiting exemplary synthetic fibers suitable for implementations of the present invention include polyethylene, polypropylene, polyesters, copolymers of polyesters and polyamides, and the like, and combinations thereof. Non-limiting exemplary wood pulps that may be used in implementations of the present invention are provided in U.S. Pat. No. 5,147,343 which is incorporated herein by reference for all purposes. The wettable fibers are generally hydrophilic or are rendered hydrophilic through a surface treatment.

In a particular implementation, the absorbent material of the invention can comprise a two phase matrix containing a first fibrous phase and a second polymer phase. The polymer should preferably form a substantially continuous phase meaning that there is sufficient number of polymer particles in the absorbent material so that a substantial number of the polymer particles are in contact with each other in the dry state, prior to absorption of any liquid. It has been generally found that for a continuous polymer phase to exist the polymer should constitute at least 70 percent by weight of the weight of the continuous phase polymer layer. Preferably, the polymer can constitute at least 80 percent by weight, and more preferably at least 90 percent by weight.

A sufficiently small quantity of wood pulp fibers can be included in order to, inter alia, maintain the stability of the adsorbent structure and preserve the wicking function of the fibers. The amount of the fibrous phase should range between about 5 percent by weight and 30 percent by weight of the total weight of the continuous Polymer phase, preferably, the fibers should not exceed 15 percent, and more preferably should not exceed 10 percent, by weight of the total weight of the absorbent material.

Figure 2A:
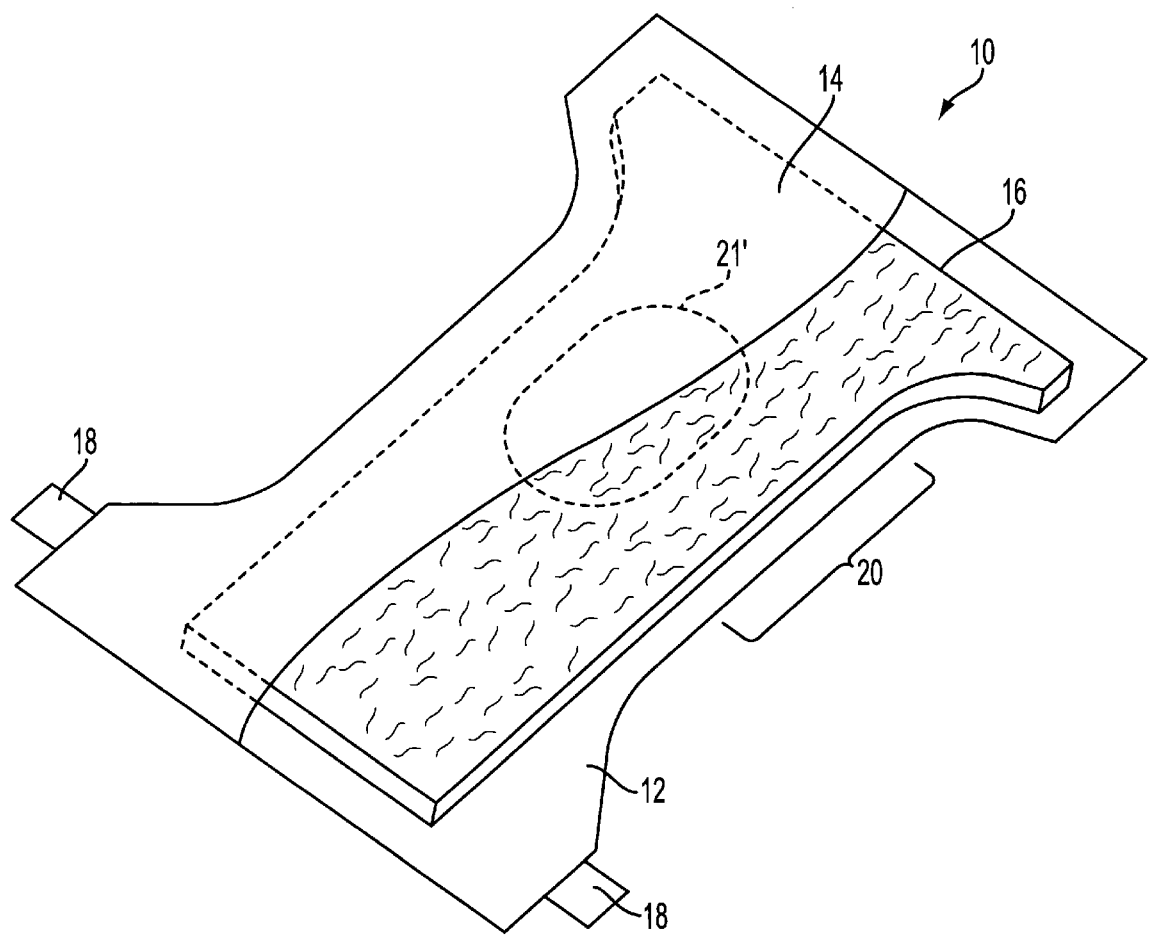
FIG. 2A is a vertical cross-sectional view of a target region 21' of the diaper shown in FIG. 2.
Figure 2B:
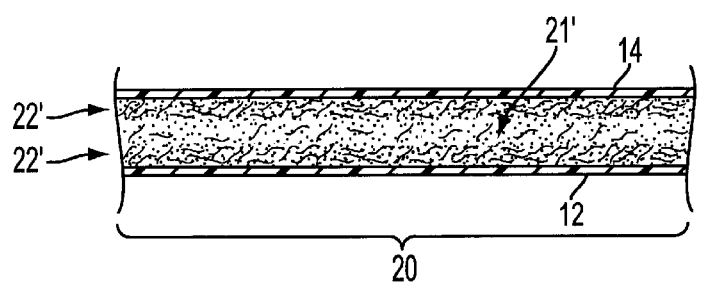
FIG. 2 is a perspective view, partially cutaway, of a disposable absorbent diaper according to an implementation of the present invention.

The present invention also provides improved disposable absorbent articles such as but not limited to diapers, sanitary napkins that incorporate the absorbent composite of the present invention. Disposable diaper articles are described in U.S. Pat. Nos. 4,673,402; 5,147,343; 5,330,822; 4,834,735; and 5,281,207, which are incorporated herein by reference for all purposes. A preferred disposable diaper, for the purpose of this invention, is shown in FIGS. 2 and 2A. In accordance with FIGS. 2 and 2A, a disposable diaper 10 comprises a liquid impermeable back sheet 12, a liquid permeable top sheet 14 and an absorbent panel structure 16 positioned between the top sheet 14 and the back sheet 12.

In accordance with the present invention, in at least a layer of the absorbent panel, in a target region thereof indicated by circle 21', taken in the Z-direction thereof (i.e., in a direction from top to bottom, away from the wearer), the superabsorbent material comprises a substantially continuous phase of the matrix. For purposes of this disclosure, the substantially continuous phase is provided wherein a sufficient quantity of particles of the superabsorbent material are in multiple point contact with each other, both prior to sorption of liquid and thereafter, to thereby define a capillary network for facilitating liquid transport within the panel structure. A sufficiently small quantity of wood pulp fibers, preferably at least about 5 percent and no more than about 30 percent on a weight percentage basis, are intermixed with the superabsorbent material in the continuous phase. This quantity of wood pulp fiber acts to maintain the stability of the absorbent structure by integrating the region of the continuous phase of superabsorbent particles with adjacent portions of the absorbent structure. As a result, the target region of the absorbent panel structure, designated 20 in FIG. 2, and which includes said layer, exhibits a free volume, at 600 seconds, of at least about 15 percent during finite volume absorbency under load (FVAUL) testing. The target region corresponds to the second and third fifths of the absorbent structure, measured from the front thereof.

As shown in the cross-sectional view FIG. 2a, the layer of the absorbent matrix having the continuous phase portion 21' is preferably positioned between two layers, designated 22', each comprising predominantly wood pulp fibers. These layers 22' each comprise at least 80 percent and preferably as much as 95 percent or more, by weight basis, of wood pulp fibers. In the case of a diaper, the liquid permeable top sheet 14 allows urine to flow through the sheet to the absorbent panel structure 16 and also keeps the baby from directly contacting the absorbent panel structure. This configuration provides more comfort for the baby and also helps to position the absorbent panel structure. Liquid permeable top sheets, and liquid impermeable back sheets, are well known to those skilled in the art, and these components can be suitably selected in practicing the present invention.

Back sheet 12 is impermeable to liquids, and thus, helps to retain a liquid so that the liquid may be absorbed and retained by the absorbent panel structure. In a baby diaper, the impermeable back sheet is typically a sheet of plastic film, such as polyethylene, that helps to retain the urine so that the urine may be absorbed by the absorbent panel structure of the diaper. For a detailed discussion of materials that can be used in the top and back sheet of a diaper, see U.S. Pat. No. 5,281,207 issued to Chmielewski, et al. and which is incorporated herein for all purposes.

The absorbent panel structure 16 is made of a two phase matrix comprising wood pulp fiber and surface crosslinked polymeric superabsorbent material. As noted above, by two phase, it is meant that the absorbent panel structure has two components, fibers (preferably wood pulp) and a superabsorbent material. The absorbent structure may comprise more than one layer. For example, the absorbent structure may have a layer that is substantially wood pulp fiber, while on top of this layer the absorbent structure may have another layer of wood pulp fiber that contains particulate superabsorbent material dispersed in the wood pulp fiber. It is contemplated that many different combinations of layers may be used in the practice of the present invention. For example, in a preferred embodiment of the invention, in at least the target region 20, a three layer system is formed in which a layer containing superabsorbent particulate material in a substantially continuous phase is positioned between adjacent layers formed predominantly of wood pulp fiber.

A greater quantity of superabsorbent material is preferably found dispersed in the wood pulp fibers in the target region 20 than in any other portion of the absorbent panel structure. In the target region 20, in at least one layer thereof, the superabsorbent material comprises a substantially continuous phase. By continuous phase, it is meant that the quantity of superabsorbent particles is so great in the region as to contact each other and to thereby define a capillary network for facilitating liquid transport within the panel structure. Thus, in the continuous phase there is more superabsorbent particles than wood pulp fibers, preferably at least 70 percent up to about 90 percent, on a weight percentage basis of superabsorbent particles. However, it should be noted that even in the continuous phase, the superabsorbent material is dispersed in the wood pulp fiber. A relatively small quantity of wood pulp fibers intermixed with the superabsorbent material is present in the continuous phase, for stability, since this small quantity of wood pulp fibers acts to integrate the continuous phase portion 21' with adjacent portions of the absorbent structure.

The continuous phase portion 21' containing superabsorbent particulate material may be substantially continuous across the entire width and length of the absorbent structure. The continuous phase portion 21' containing superabsorbent material is preferably located in specific targeted areas within the absorbent structure, such a target region 20, extended along a longitudinal centerline of the absorbent structure for at least the second and third fifths of the length of the absorbent structure. The continuous phase portion 21' can extend outwardly from the longitudinal centerline toward the side marginal edges of the article at least 20 percent–100 percent of the width of the absorbent structure, and preferably about 50 percent–70 percent. Because superabsorbent material is one of the most costly components of an absorbent structure, efficient use and positioning of the material is beneficial. Specific positioning of the superabsorbent material in areas most likely to be insulted with urine allows for the most cost effective utilization of this component. Specific positioning of superabsorbent material can be accomplished through any of several methods, such as by the method and apparatus as described and claimed in U.S. Pat. No. 5,279,854, which is incorporated herein by reference. This specific positioning creates a target region 20 shown in FIG. 2.

As noted, FIG. 1 is a pictorial representation of a portion of the absorbent matrix wherein the substantially continuous phase comprises particulate superabsorbent material 21, wood pulp fibers 22, and interstitial voids or free volume 23. As FIG. 1 shows, the particles of superabsorbent material touch and the interstitial voids of spaces between the particles and fibers is called the free volume. The free volume is important as the free volume space is necessary to maintaining a capillary structure through which the liquid can be transported and stored. Thus, the amount of free volume in an absorbent structure is important to the absorbency characteristics of the continuous phase. The continuous phase may be described as a region of the absorbent structure wherein there is so much superabsorbent as to make the amount of wood pulp fiber appear relatively small in comparison.

While not wishing to be bound by any particular theory, it is thought that gel blocking is ameliorated, despite the use a large quantity of superabsorbent material that forms a continuous phase, because rather that losing their shape, and therefore contacting each other to the exclusion of free volume, the crosslinked particulate superabsorbent material swells, but maintains a particular shape. Thus, as the superabsorbent particles swell, rather than coalescing with adjacent swollen particles, the particles contact and push against each other and thereby maintain free volume and a capillary structure or network through which liquid may be transported to that superabsorbent material that has not absorbed a liquid. In addition to maintaining their shape, the volume of the section of the absorbent panel containing the continuous phase of superabsorbent particles increases markedly.

In addition, because the superabsorbent particles retain their shape and do not coalesce as a gel, the amount of free volume (as hereinafter defined) is not diminished greatly. Preferably, the free volume of the target region, at 600 seconds, during finite volume absorbency under load (FVAUL) testing is at least about 15 percent, and preferably at least about 20 percent, more preferably at least about 25 percent and most preferably at least about 30 percent. As noted, the target region 20 is generally located in the second and third fifths of the panel length, measured from the front of the diaper, and preferably comprises a top layer 22' predominantly of wood pulp fiber, a bottom layer 22' predominantly of wood pulp fiber and a middle layer that contains the continuous phase 21' of superabsorbent particles, in an amount ranging from about 70 percent to about 95 percent, preferably from about 80 percent to about 90 percent of the total weight of fibers and superabsorbent particles.

The present invention is also directed to a method and apparatus for calculating the FVAUL free volume of an absorbent composite comprising a surface crosslinked polymer material and wettable fibers. The present invention apparatus comprises a cylindrical open top holder for receiving a sample of the composite therein. A cylindrical weight having a screen secured at its bottom surface and a slot on one of its other surfaces is placed on top of the sample. The slot is in fluid communication with the screen at the bottom of the weight. As liquid is poured into the slot, it is evenly distributed through the screen on the top surface of the sample inside the holder. The apparatus further comprises means for holding the weight in place while allowing the weight to expand freely in a direction that is perpendicular to the top surface of the sample upon absorbing the liquid. An LVDT device is operatively connected to said sample in order to measure the sample expansion. The LVDT device has rods that hold the weight in place on top of the sample. The holders, with the sample and the weight, are placed on top of a weight balance which measures the weight of the sample. The weight balance and LVDT devices are operatively connected to a computer. The data collected from the balance weight and the LVDT device are fed into the computer which calculates a free volume value at various time intervals from the time of the liquid addition.

Specifically, the method of calculating the free volume of the absorbent composite comprises placing a sample inside the holder, positioning a weight on top of the sample and pouring a liquid on the top surface of the sample through the weight slot. The liquid is evenly distributed on the top surface of the sample by the screen that is secured at the bottom of the weight. The sample is die-cut from the absorbent composite so that it has a cross section that matches the cross section of the holder and a volume about equal to the internal volume of the holder. The sample will thus tightly fit inside the sample holder. The method further consists of measuring the volume of the sample, measuring the mass of the sample using the weight balance, feeding said measured volume and mass values to a computer and calculating the free volume of the sample according to the equation.

$$FV_S = V_S - R^* w/\rho_{SAP} M - (1-R)^* W/\rho_{PULP}$$

wherein $FV_S$ is the free volume of the sample, $V_S$ is the volume of the sample, R is the weight ratio of SAP to sample weight, $\rho_{SAP}$ is the density of the SAP, $\rho_{pulp}$ is the density of the pulp, and W is the mass of the sample and wherein R, $\rho_{SAP}$, and $\rho_{pulp}$ are known values fed into the computer.

Test Method
Finite Volume Absorbency Under Load Method (FVAUL)

Two inch diameter samples of absorbent composites comprising wood pulp fiber and surface crosslinked superabsorbent material were die cut out of the cores of the absorbent article to be tested. The samples were equilibrated in a TAPPI conditioned room for 16 hours, and then placed in the holder 36 of the apparatus of FIG. 3.

Figure 3:
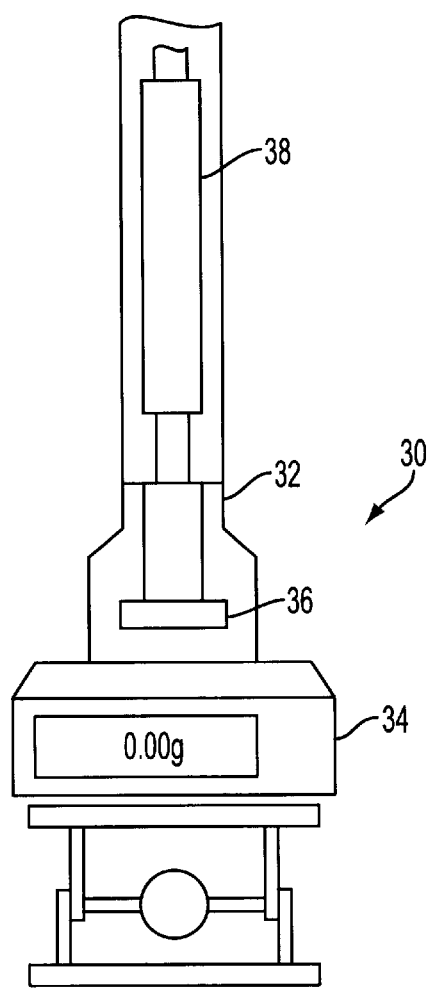
FIG. 3 is a diagrammatic view of an apparatus used to measure FVAUL according to an implementation of the present invention.
Figure 4:
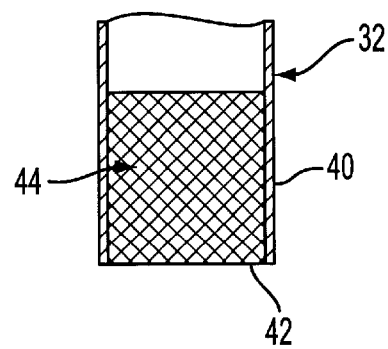
FIG. 4 shows a close-up view of a weight used in measuring FVAUL according to an implementation of the present invention.
Figure 5:
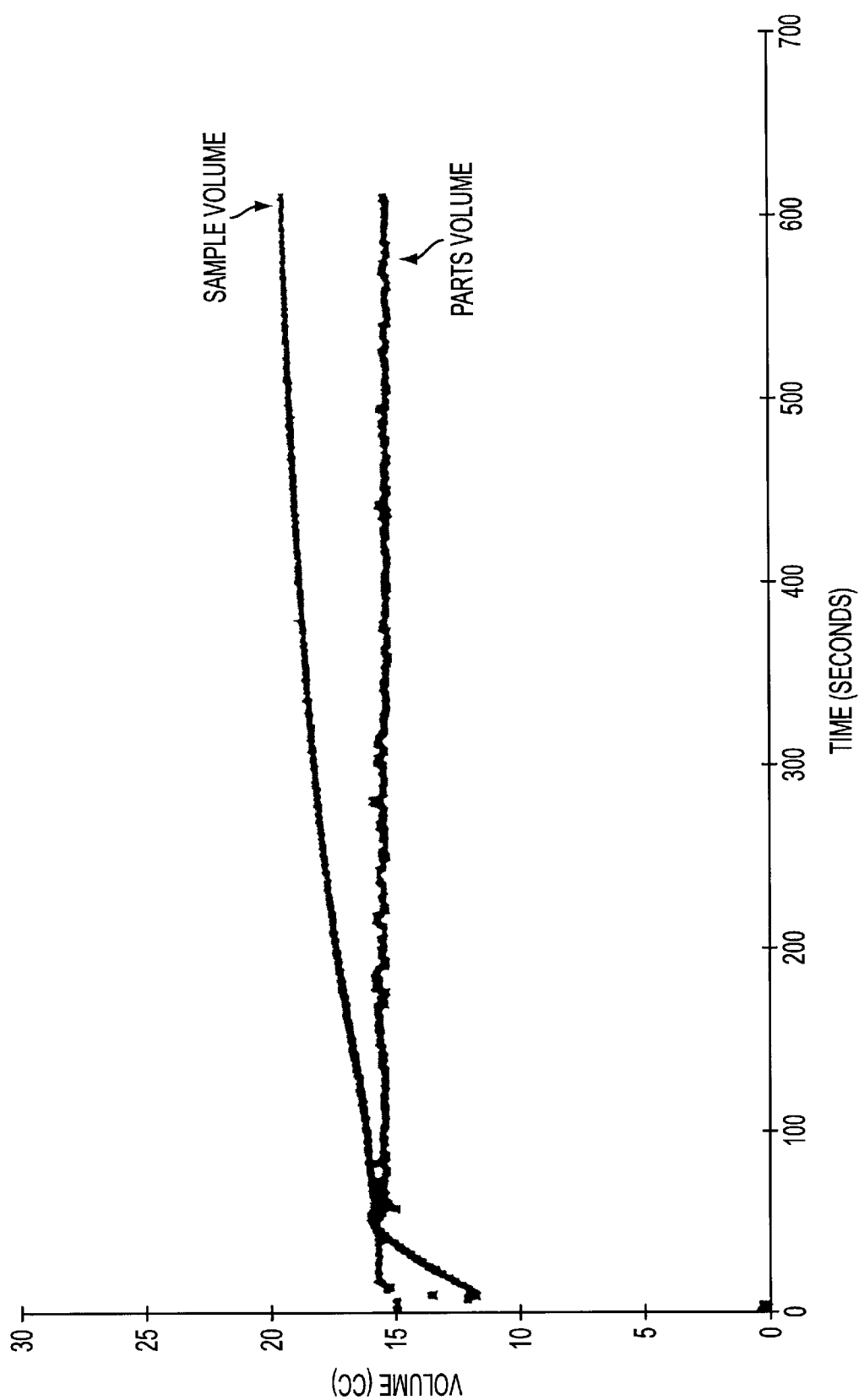
FIG. 5 is a graphical presentation of FVAUL test data showing data obtained in Test No. 1 of Table 2.
Figure 6:
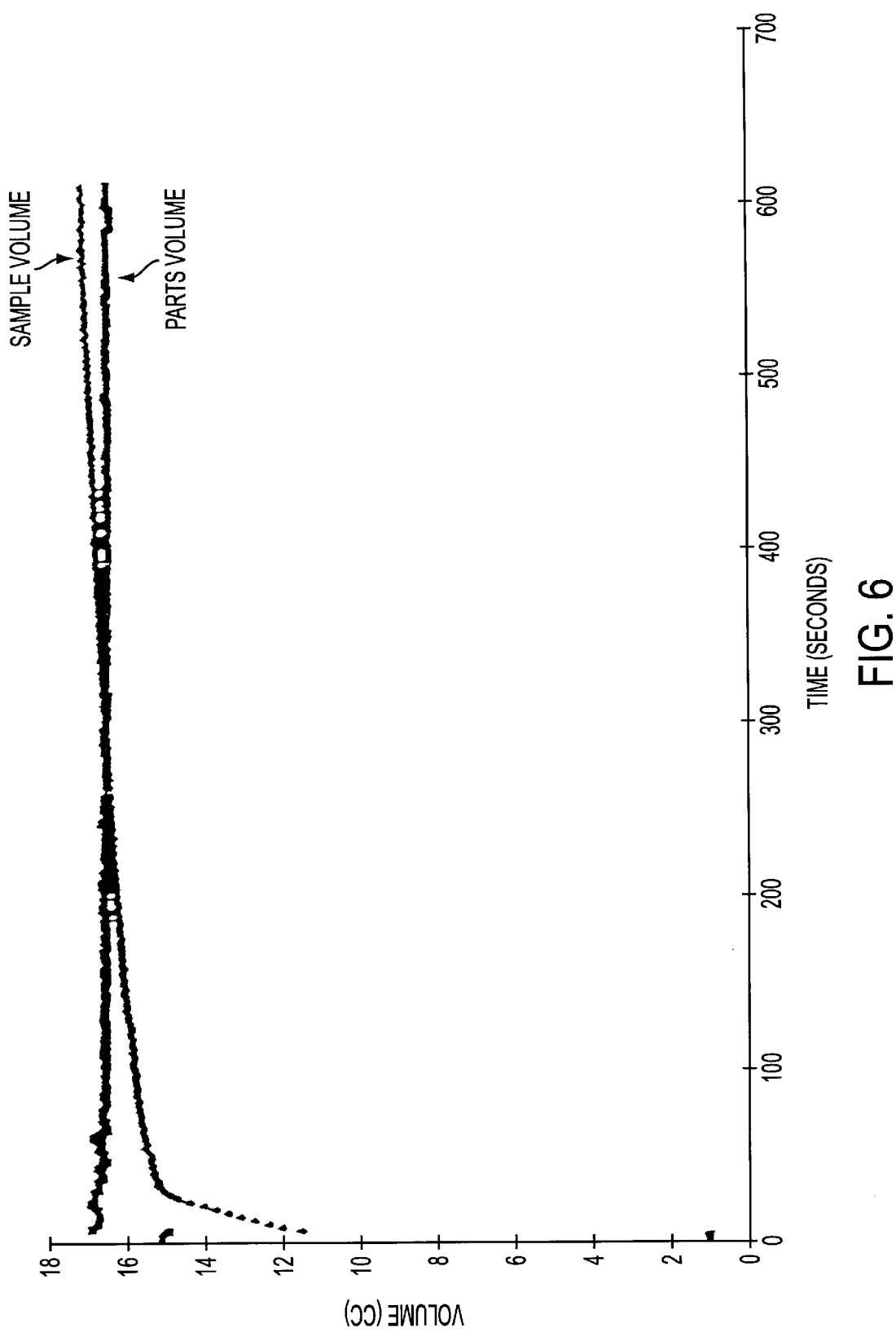
FIG. 6 is a graphical presentation of FVAUL test data showing data obtained in Test No. 5 of Table 1.
Figure 7:
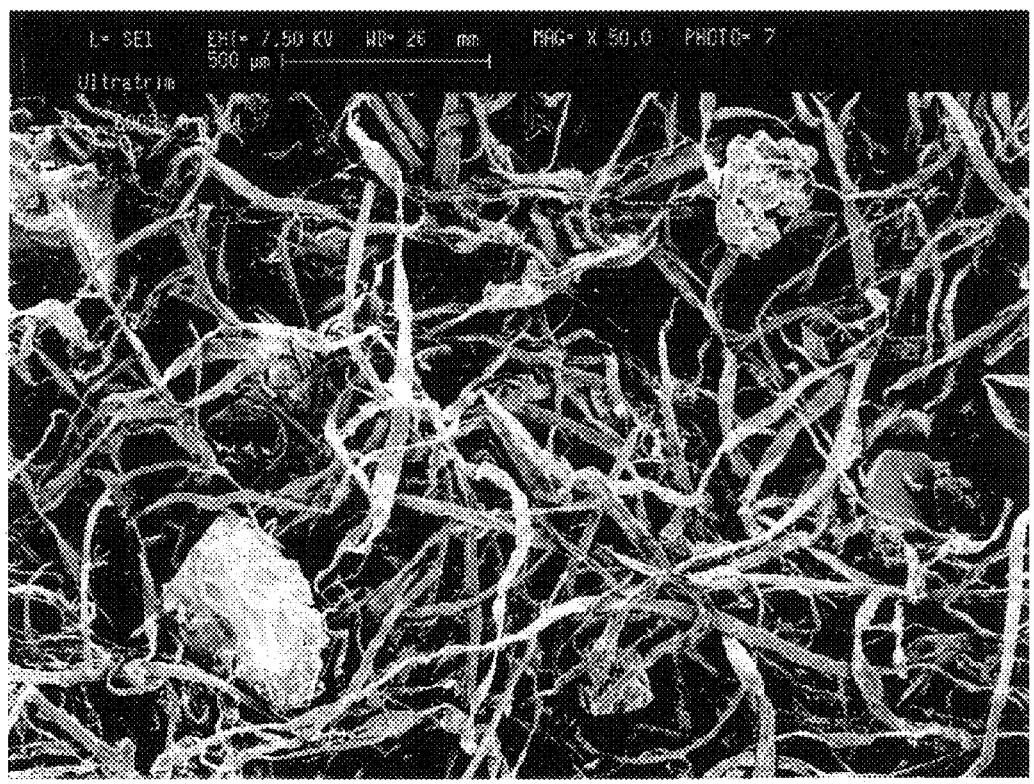
FIGS. 7 and 8 are photomicrographs of specific implementations of the absorbent composites in accordance with the present invention.
Figure 8:
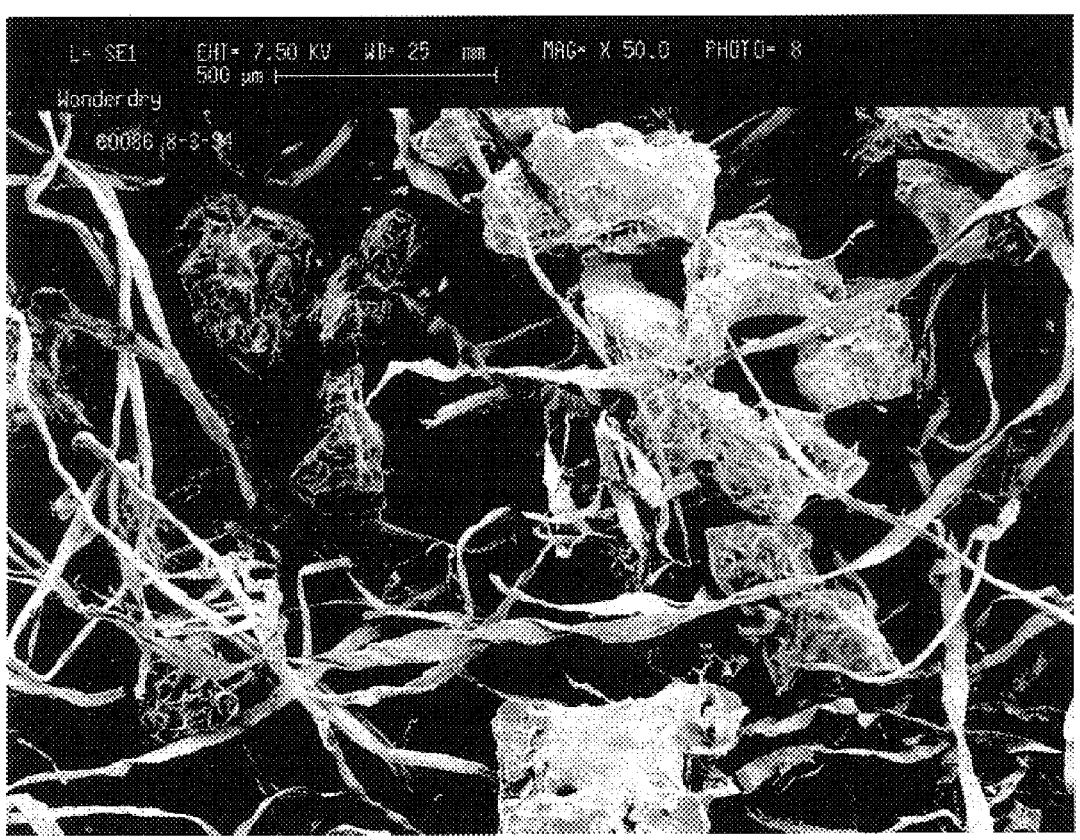
Figure 9:
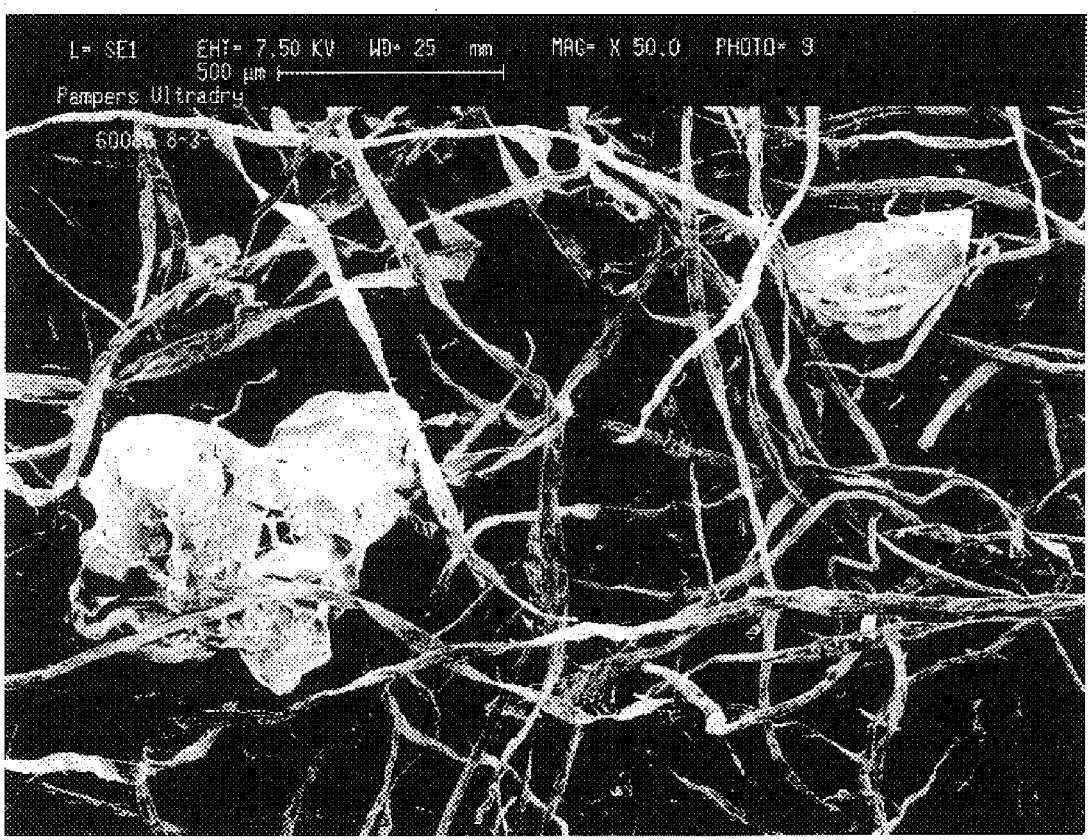
FIG. 9 is a photomicrograph of an absorbent composite prepared using conventional methods, provided for comparative purposes.

FIG. 3 shows an apparatus used to measure finite volume absorbency under load (FVAUL), while FIG. 4 shows a close up view of a weight 32 used in the FVAUL testing. The apparatus includes balance 34 and a sample holder 36 positioned on the balance, with the weight 32 configured for positioning on a test sample held by the sample holder. An LVDT (linear variable differential transducer) measuring system 38 is positioned to engage the weight 32 and measure its movement as a finite volume of liquid is introduced into the sample holder for absorption by a test sample. A Lucas Schaevitz Type 2000 HPA LVDT system was employed, which employed Lucas Schaevitz System 96 software. Since this software only provides LVDT measurements, additional software was provided to obtain readouts of values from balance 34, and of time.

As shown in FIG. 4, the weight 32 includes a stainless steel tube 40 and a bottom stainless steel screen 42, with stainless steel slot 44 held within the tube and screen. Liquid to be introduced into a test sample is poured through the steel slot so that it passes through the screen 42 into the sample holder 36.

A computer software that can run the LVDT (linear variable differential transducer) system was booted. The LVDT system was calibrated, and the computer program to run the test was booted. 300 data sets were taken at two second intervals. A data set consists of time to the nearest hundredth second, balance reading to the nearest hundredth gram, and the LVDT reading to the nearest hundredth inch. The sample holder and a 0.16 psi porous weight were cleaned and then the holder was placed on a balance and the weight was put into place. The LVDT rods were then placed on the weights and the LVDT was zeroed.

The LVDT and the weight were removed and weighed and then the sample was placed into the holder (baby side up). The weight and LVDT were replaced and the computer program calculated the sample's thickness. The computer program asked for the sample weight and the ratio of superabsorbent particles (SAP) to sample weight. This information was used to determine the total volume being taken up by the SAP and pulp in the sample. The densities of 1.5 for SAP and 1.7 for pulp are used by the program. The computer the "calculates the free volume of the sample when dry. (If this value is known to be incorrect because of pad construction, it is possible to re-enter the free volume.)

An air shield was placed around the sample tester and the balance was zeroed (tared). 15 ml of test solution of 1 percent sodium chloride in water was prepared and placed in a graduated cylinder. The computer was then activated to start taking data sets and was allowed to take two data points before the solution was added. These two data sets are used to calculate the initial volume of the sample in the dry state. The 15 ml solution was quickly poured into the weight and was absorbed through the screen in the bottom of the weight into the sample. After the computer had taken 300 data sets, the computer generates the desired data such as dry free volume (the amount of air in the sample), the sample volume and sample mass as a function of time. The volume of the parts of the sample is calculated by taking the dry sample volume and subtracting the free volume from it and then adding the volume of liquid added.

$Volume_{parts} = (V_d - V_f) + L/1.01$
$V_d$ = Volume of Dry sample
$V_f$ = free volume of air
$L$ = weight of the liquid
$1.01$ = density of 1% NaCl solution.

The sample volume and the volume by parts at 60 seconds and at 600 seconds was recorded.

The computer program that reads information from the LVDT system and the balance calculates the free volume for the dry sample and records that as the first record in the computer file. The calculation is based on three pieces of information: the sample weight, the ratio of superabsorbent to sample weight, and the sample thickness. The samples are all assumed to be two inches in diameter. The following equation shows how the calculation is done.

| | |
|---|---|
| | $FV_s$ = Free Volume |
| | $\rho_{sap}$ = Density of SAP (g/(cm$^3$)) |
| | $\rho_{pulp}$ = Density of pulp (g/(cm$^3$)) |
| | W = Mass of Sample (g) |
| | R = Ratio of SAP to Sample Weight (g/g) |
| $M_{sap} = R \cdot W$ | $T_s$ = Thickness of the Sample (cm) |

The following is the complete equation. 1.5 g/cc is used for the density of the superabsorbent 1.7 g/cc is used for the density of the pulp.

$$FV_s = 20.268 \cdot T_s - [R \cdot W/\rho_{sap}] - [(1-R) \cdot W/\rho_{pulp}]$$

The present invention has been described in connection with the preferred embodiments. These embodiments, however, are merely for example and the invention is not restricted thereto. Any examples described herein are illustrative of preferred embodiments of the inventive subject matter and are not to be construed as limiting the inventive subject matter thereto. It will be understood by those skilled in the art that other variations and modifications can easily be made within the scope of the invention as defined by the appended claims.

What is claimed is:

1. An absorbent composition comprising:
   about 5% by weight to about 30% by weight of a fibrous matrix comprising wettable fibers;
   about 70% by weight to about 95% by weight of a surface crosslinked polymer, said surface crosslinked polymer being disbursed within said fibrous matrix;
   wherein the absorbent composition has a Finite Volume Absorbency Under Load FVAUL value of at least about 60 cc after 10 minutes, said FVAUL value being determined by the formula $FV_s = 20.268 \cdot T_s - [R \cdot W/\rho_{sap}] - [(1-R) \cdot W/\rho_{pulp}]$; and $T_s$ is thickness of the sample (cm), R is ratio of SAP to sample weight (g/g), W is mass of the sample (g), $\rho_{sap}$ is density of SAP (g/cm$^3$), and $\rho_{pulp}$ is density of pulp(g/cm$^3$).

2. The absorbent composition of claim 1, wherein the surface crosslinked polymer is bipolar.

3. The absorbent composition of claim 1, wherein the surface crosslinked polymer provides minimal gel-blocking properties upon absorption of liquid.

4. The absorbent composition of claim 1, wherein the surface crosslinked polymer constitutes about 85% by weight to about 95% by weight of the combined weight of the fiberous matrix and the surface crosslinked polymer.

5. The absorbent composition of claim 1, wherein the surface crosslinked polymer constitutes about 90% by weight to about 95% by weight of the combined weight of the fiberous matrix and the surface crosslinked polymer.

6. The absorbent composition of claim 1, wherein said wettable fibers constitute about 5% by weight to about 15% by weight of the combined weight of the fiberous matrix and the surface crosslinked polymer.

7. The absorbent composition of claim 1, wherein said wettable fibers constitute about 5% by weight to about 10% by weight of the combined weight of the fiberous matrix and the surface crosslinked polymer.

8. The absorbent composition of claim 1, wherein the surface crosslinked polymer comprises a mixed-bed ion-exchange superabsorbent polymer composition.

9. The absorbent composition of claim 1, wherein the FVAUL free volume of the absorbent composition is about 20% to about 70%.

10. The absorbent composition of claim 1, wherein the FVAUL free volume of the absorbent composition is about 20% to about 60%.

11. The absorbent composition of claim 1, wherein the FVAUL free volume of the absorbent composition is about 20% to about 50%.

12. The absorbent composition of claim 1, wherein the FVAUL free volume of the absorbent composition is about 25% to about 50%.

13. The absorbent composition of claim 1, wherein the surface crosslinked polymer is evenly disbursed within the fibrous matrix.

14. The absorbent composition of claim 1, wherein the surface crosslinked polymer is poly(acrylic acid).

15. The absorbent composition of claim 1, wherein the surface crosslinked polymer comprises about 95% by weight of poly(acrylic acid) and about 3% by weight of a crosslinking agent.

16. The absorbent composition of claim 15, wherein the crosslinking agent is methylene bisacrylamide.

17. The absorbent composition of claim 15, wherein the surface crosslinked polymer additionally comprises a neutralizing agent.

18. The absorbent composition of claim 17, wherein the neutralizing agent is triethanol amine.

19. The absorbent composition of claim 1, wherein the wettable fibers are selected from the group consisting of natural fibers, synthetic fibers, and combinations thereof.

20. The absorbent composition of claim 1, wherein the wettable fibers are selected from the group consisting of wood pulp (fluff), cotton linters, polyethylene, polypropylene, polyesters, copolymers of polyesters and polyamides, and combinations thereof.

21. The absorbent composition of claim 1, wherein the wettable fibers are selected from the group consisting of wood pulp fibers, meltblown synthetic fibers and combinations thereof.

22. An absorbent composition prepared by the process comprising:
providing a first layer of wettable fibers;
distributing on the first layer of wettable fibers a layer of surface crosslinked polymer;
providing a second layer of wettable fibers on top of the layer of surface crosslinked polymer; and
calendaring said layers to form the wettable fibers into a fibrous matrix having the surface crosslinked polymer disbursed therein, said surface crosslinked polymer comprising about 70% by weight to about 95% by weight the absorbent composition and said wettable fibers comprising about 5% by weight to about 30% by weight of the absorbent composition, said absorbent composition having a Finite Volume Absorbency Under Load (FVAUL) value of at least about 60 cc after 10 minutes, said FVAUL value being determined by Finite Volume Absorbency Under Load Method.

23. The absorbent composition of claim 22, wherein the surface crosslinked polymer is bipolar.

24. The absorbent composition of claim 22, wherein the surface crosslinked polymer provides minimal gel-blocking properties upon absorption of liquid.

25. The absorbent composition of claim 22, wherein the surface crosslinked polymer constitutes about 85% by weight to about 95% by weight of the combined weight of the fiberous matrix and the surface crosslinked polymer.

26. The absorbent composition of claim 22, wherein the surface crosslinked polymer constitutes about 90% by weight to about 95% by weight of the combined weight of the fiberous matrix and the surface crosslinked polymer.

27. The absorbent composition of claim 22, wherein said wettable fibers constitute about 5% by weight to about 15% by weight of the combined weight of the fiberous matrix and the surface crosslinked polymer.

28. The absorbent composition of claim 22, wherein said wettable fibers constitute about 5% by weight to about 10% by weight of the combined weight of the fiberous matrix and the surface crosslinked polymer.

29. The absorbent composition of claim 22, wherein the surface crosslinked polymer comprises a mixed-bed ion-exchange superabsorbent polymer composition.

30. The absorbent composition of claim 22, wherein the FVAUL free volume of the absorbent composition is about 20% to about 70%.

31. The absorbent composition of claim 22, wherein the FVAUL free volume of the absorbent composition is about 20% to about 60%.

32. The absorbent composition of claim 22, wherein the FVAUL free volume of the absorbent composition is about 20% to about 50%.

33. The absorbent composition of claim 22, wherein the FVAUL free volume of the absorbent composition is about 25% to about 50%.

34. The absorbent composition of claim 22, wherein the surface crosslinked polymer is evenly disbursed within the fibrous matrix.

35. The absorbent composition of claim 22, wherein the surface crosslinked polymer is poly(acrylic acid).

36. The absorbent composition of claim 22, wherein the surface crosslinked polymer comprises about 95% by weight of poly(acrylic acid) and about 3% by weight of a crosslinking agent.

37. The absorbent composition of claim 36, wherein the crosslinking agent is methylene bisacrylamide.

38. The absorbent composition of claim 36, wherein the surface crosslinked polymer additionally comprises a neutralizing agent.

39. The absorbent composition of claim 38, wherein the neutralizing agent is triethanol amine.

40. The absorbent composition of claim 22, wherein the wettable fibers are selected from the group consisting of natural fibers, synthetic fibers, and combinations thereof.

41. The absorbent composition of claim 22, wherein the wettable fibers are selected from the group consisting of wood pulp (fluff), cotton linters, polyethylene, polypropylene, polyesters, copolymers of polyesters and polyamides, and combinations thereof.

42. The absorbent composition of claim 22, wherein the wettable fibers are selected from the group consisting of wood pulp fibers, meltblown synthetic fibers and combinations thereof.

43. An absorbent composition comprising:
a surface crosslinked polymer;
wherein the absorbent composition has a Finite Volume Absorbency Under Load FVAUL value of at least about 60 cc after 10 minutes, said FVAUL value being determined by the formula $FV_s=20.268 \cdot T_s-[R \cdot W/\rho_{sap}]-[(1-R) \cdot W/\rho_{pulp}]$; and $T_s$ is thickness of the sample (cm), R is ratio of SAP to sample weight (g/g), W is mass of the sample (g), $\rho_{sap}$ is density of SAP (g/cm$^3$), and $\rho_{pulp}$ is density of pulp(g/cm$^3$).

44. An absorbent article comprising:
a permeable topsheet;
a substantially impermeable backsheet; and
an absorbent core disposed between the permeable topsheet and the substantially impermeable backsheet, said absorbent core comprising an absorbent composition comprising about 5% by weight to about 30% by weight of a fibrous matrix comprising wettable fibers and about 70% by weight to about 95% by weight of a surface crosslinked polymer, said surface crosslinked polymer being disbursed within said fibrous matrix;
wherein the absorbent composition has a Finite Volume Absorbency Under Load FVAUL value of at least about 60 cc after 10 minutes, said FVAUL value being determined by the formula $FV_s=20.268 \cdot T_s-[R \cdot W/\rho_{sap}]-[(1-R) \cdot W/\rho_{pulp}]$; and $T_s$ is thickness of the sample (cm), R is ratio of SAP to sample weight (g/g), W is mass of the sample (g), $\rho_{sap}$ is density of SAP (g/cm$^3$), and $\rho_{pulp}$ is density of pulp(g/cm$^3$).

45. The absorbent article of claim 44, wherein the surface crosslinked polymer is bipolar.

46. The absorbent article of claim 44, wherein the surface crosslinked polymer provides minimal gel-blocking properties upon absorption of liquid.

47. The absorbent article of claim 44, wherein the surface crosslinked polymer constitutes about 85% by weight to about 95% by weight of the combined weight of the fiberous matrix and the surface crosslinked polymer.

48. The absorbent article of claim 44, wherein the surface crosslinked polymer constitutes about 90% by weight to about 95% by weight of the combined weight of the fiberous matrix and the surface crosslinked polymer.

49. The absorbent article of claim 44, wherein said wettable fibers constitute about 5% by weight to about 15% by weight of the combined weight of the fiberous matrix and the surface crosslinked polymer.

50. The absorbent article of claim 44, wherein said wettable fibers constitute about 5% by weight to about 10% by weight of the combined weight of the fiberous matrix and the surface crosslinked polymer.

51. The absorbent article of claim 44, wherein the surface crosslinked polymer comprises a mixed-bed ion-exchange superabsorbent polymer composition.

52. The absorbent article of claim 44, wherein the FVAUL free volume of the absorbent composition is about 20% to about 70%.

53. The absorbent article of claim 44, wherein the FVAUL free volume of the absorbent composition is about 20% to about 60%.

54. The absorbent article of claim 44, wherein the FVAUL free volume of the absorbent composition is about 20% to about 50%.

55. The absorbent article of claim 44, wherein the FVAUL free volume of the absorbent composition is about 25% to about 50%.

56. The absorbent article of claim 44, wherein the surface crosslinked polymer is evenly disbursed within the fibrous matrix.

57. The absorbent article of claim 44, wherein the surface crosslinked polymer is poly(acrylic acid).

58. The absorbent article of claim 44, wherein the surface crosslinked polymer comprises about 95% by weight of poly(acrylic acid) and about 3% by weight of a crosslinking agent.

59. The absorbent article of claim 58, wherein the crosslinking agent is methylene bisacrylamide.

60. The absorbent article of claim 58, wherein the surface crosslinked polymer additionally comprises a neutralizing agent.

61. The absorbent article of claim 60, wherein the neutralizing agent is triethanol amine.

62. The absorbent article of claim 44, wherein the wettable fibers are selected from the group consisting of natural fibers, synthetic fibers, and combinations thereof.

63. The absorbent article of claim 44, wherein the wettable fibers are selected from the group consisting of wood pulp (fluff), cotton linters, polyethylene, polypropylene, polyesters, copolymers of polyesters and polyamides, and combinations thereof.

64. The absorbent article of claim 44, wherein the wettable fibers are selected from the group consisting of wood pulp fibers, meltblown synthetic fibers and combinations thereof.

65. The absorbent article of claim 44, wherein the absorbent article is a nighttime diaper.

66. The absorbent article of claim 44, wherein the absorbent article is a long-term use diaper.

67. The absorbent article of claim 44, wherein the absorbent article is a travel diaper.

68. An absorbent composition comprising:
about 5% by weight to about 30% by weight of a fibrous matrix comprising wettable fibers;
about 70% by weight to about 95% by weight of a surface crosslinked polymer, said surface crosslinked polymer being disbursed within said fibrous matrix;
wherein the absorbent composition has a Finite Volume Absorbency Under Load (FVAUL) value of at least about 60 cc after 10 minutes, said FVAUL value being determined by the formula $FV_s=20.268 \cdot T_s-[R \cdot W/\rho_{sap}]-[(1-R) \cdot W/\rho_{pulp}]$; and $T_s$ is thickness of the sample (cm), R is ratio of SAP to sample weight (g/g), W is mass of the sample (g), $\rho_{sap}$ is density of SAP (g/cm$^3$), and $\rho_{pulp}$ is density of pulp(g/cm$^3$);
wherein the surface crosslinked polymer comprises about 95% by weight of poly(acrylic acid) and about 3% by weight of a crosslinking agent; and
wherein the surface crosslinked polymer additionally comprises a neutralizing agent; said neutralizing agent is triethanol amine.

69. An absorbent composition prepared by the process comprising:
providing a first layer of wettable fibers;

distributing on the first layer of wettable fibers a layer of surface crosslinked polymer;

providing a second layer of wettable fibers on top of the layer of surface crosslinked polymer; and calendaring said layers to form the wettable fibers into a fibrous matrix having the surface crosslinked polymer disbursed therein, said surface crosslinked polymer comprising about 70% by weight to about 95% by weight the absorbent composition and said wettable fibers comprising about 5% by weight to about 30% by weight of the absorbent composition, said absorbent composition having a Finite Volume Absorbency Under Load (FVAUL) value of at least about 60 cc after 10 minutes, said FVAUL value being determined by Finite Volume Absorbency Under Load Method;

wherein the surface crosslinked polymer comprises about 95% by weight of poly(acrylic acid) and about 3% by weight of a crosslinking agent; and wherein the surface crosslinked polymer additionally comprises a neutralizing agent, said neutralizing agent being triethanol amine.

70. An absorbent article comprising:

a permeable topsheet;

a substantially impermeable backsheet; and an absorbent core disposed between the permeable topsheet and the substantially impermeable backsheet, said absorbent core comprising an absorbent composition comprising about 5% by weight to about 30% by weight of a fibrous matrix comprising wettable fibers and about 70% by weight to about 95% by weight of a surface crosslinked polymer, said surface crosslinked polymer being disbursed within said fibrous matrix;

wherein the absorbent composition has a Finite Volume Absorbency Under Load (FVAUL) value of at least about 60 cc after 10 minutes, said FVAUL value being determined by the formula $FV_s = 20.268 \cdot T_s - [R \cdot W/\rho_{sap}] - [(1-R) \cdot W/\rho_{pulp}]$; and $T_s$ is thickness of the sample (cm), R is ratio of SAP to sample weight (g/g), W is mass of the sample (g), $\rho_{sap}$ is density of SAP (g/cm$^3$), and $\rho_{pulp}$ is density of pulp(g/cm$^3$);

wherein the surface crosslinked polymer comprises about 95% by weight of poly(acrylic acid) and about 3% by weight of a crosslinking agent; and wherein the surface crosslinked polymer additionally comprises a neutralizing agent, said neutralizing agent being triethanol amine.

* * * * *